(12) United States Patent
Khachatoorian et al.

(10) Patent No.: US 6,238,212 B1
(45) Date of Patent: May 29, 2001

(54) METHOD AND APPARATUS FOR APPLYING A BONDING AGENT TO AN ORTHODONTIC BAND

(75) Inventors: Armineh Khachatoorian, La Crescenta; Joan V. Brennan, Sierra Madre; John S. Kelly, Arcadia; Kenneth E. Hoevel, Monrovia; Russell A. Jordan, Rancho Cucamonga, all of CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/311,245

(22) Filed: May 13, 1999

(51) Int. Cl.[7] ..................................... A61C 5/04
(52) U.S. Cl. .............................. 433/89; 433/23; 433/90
(58) Field of Search .................... 433/90, 89, 23

(56) References Cited

U.S. PATENT DOCUMENTS

| | | | |
|---|---|---|---|
| 4,492,576 | 1/1985 | Dragan | 433/90 |
| 4,538,920 | 9/1985 | Drake | 366/177 |
| 4,619,613 | 10/1986 | Dragan | 433/90 |
| 4,969,816 | 11/1990 | Drumm | 433/90 |
| 4,972,969 | 11/1990 | Randklev | 222/1 |
| 5,122,057 | 6/1992 | Discko, Jr. | 433/90 |
| 5,286,257 | 2/1994 | Fischer | 604/82 |
| 5,445,523 | 8/1995 | Fischer et al. | 433/90 |
| 5,692,642 | 12/1997 | Brattesani | 222/1 |
| 5,707,234 | * 1/1998 | Bender | 433/90 |
| 5,743,436 | 4/1998 | Wilcox et al. | 222/137 |
| 5,846,075 | * 12/1998 | Suh et al. | 433/23 |

FOREIGN PATENT DOCUMENTS

| | | |
|---|---|---|
| 8423482 | 5/1985 | (DE) . |
| WO 97/26041 | 7/1997 | (WO) . |

* cited by examiner

Primary Examiner—John J. Wilson
(74) Attorney, Agent, or Firm—James D. Christoff

(57) ABSTRACT

A syringe assembly for applying a bonding agent to an inner surface of an orthodontic band includes a syringe and a hollow dispensing tip. The dispensing tip is detachably coupled to the syringe and is discarded after each patient, so that the risk of cross-contamination is substantially reduced. The dispensing tip provides a convenient extension of the syringe and facilitates application of the bonding agent in a continuous ribbon directly onto an inner surface of the orthodontic band without the use of an auxiliary hand instrument such as a spatula or the like.

10 Claims, 2 Drawing Sheets

METHOD AND APPARATUS FOR APPLYING A BONDING AGENT TO AN ORTHODONTIC BAND

BACKGROUND OF THE INVENTION

1. Field of the Invention

This invention relates to a method and apparatus for applying a bonding agent such as an orthodontic cement or adhesive to an inner surface of an orthodontic band prior to installation of the band on a patient's tooth.

2. Description of the Related Art

Orthodontic treatment involves movement of malpositioned teeth to orthodontically correct locations for improved occlusion and appearance. One type of orthodontic treatment includes the use of tiny, slotted brackets that are connected to the patient's teeth, along with an archwire that is fitted into the slot of each bracket. The archwire forms a track to guide movement of the teeth to desired positions. In this type of treatment, the ends of the archwires are often captured in small appliances known as buccal tubes that are secured to the patient's molar teeth.

In many instances, orthodontic brackets are fixed to the patient's teeth using a technique known as direct bonding, wherein a small amount of adhesive is used to secure the base of the bracket directly to the tooth enamel. However, in some instances directly bonded brackets are not used. For example, one or more of the patient's teeth may be covered with a porcelain crown or have a front surface with a restorative material that prevents a strong bond to a bracket with the adhesives that the practitioner prefers to use. In other instances, the practitioner may simply prefer to use bands for all of the teeth receiving a bracket in accordance with his or her treatment philosophy.

Additionally, it is common practice to avoid bonding brackets or buccal tubes directly to the patient's molar teeth. The molar teeth have relatively large roots and are often used as an anchor for moving the other, smaller teeth to desired positions along the dental arch. As a consequence, the brackets and buccal tubes connected to the patient's molar teeth often are subjected to relatively large forces that may exceed the bond strength exhibited by brackets and buccal tubes that are directly bonded to the molar teeth.

Brackets and buccal tubes that spontaneously debond from the associated teeth during the course of treatment represent a substantial nuisance, since the progress of treatment is then interrupted. At that time, the patient should return to the orthodontist so that the brackets and/or buccal tubes can be rebonded, or replaced and rebonded as necessary. This procedure represents a waste of time and expense for both the orthodontist as well as for the patient, and is preferably avoided if at all possible.

As a result, orthodontic bands are often used by practitioners for at least some of the teeth of each patient. An orthodontic band is a thin, annular-shaped strip of metal alloy such as stainless steel that encircles the patient's tooth. The band serves as a secure mounting platform for a bracket or buccal tube, which is conventionally welded or brazed to the band before installation of the band on the patient's tooth.

However, it is important that the selected band fit tightly on the patient's tooth so that the band does not become loose or detached from the tooth during the course of treatment. Since teeth vary widely in size and configuration, the practitioner will often retain a wide variety of bands on hand in order to ensure that a band that properly fits is available when needed. Typically, the practitioner will trial fit two or three differently-sized bands on the tooth and then select the band that fits the best.

Once the band has been selected and the appliance (such as a bracket or buccal tube) is secured to the band, the band is mounted on the patient's designated tooth. Generally, a small layer or ribbon of orthodontic adhesive or cement is applied to the entire inner peripheral surface of the band prior to placing the band on the tooth. The adhesive or cement serves two functions: (1) to increase the strength of the bond between the band and the tooth; and (2) to fill any small gaps or voids between the band and the tooth in order to eliminate space that might otherwise collect food or other debris and facilitate formation of caries.

Conventional bonding agents such as adhesives and cements that are used for orthodontic banding are often supplied by the manufacturer in a bulk syringe for use with a multiple number of bands and a multiple number of patients. However, such syringes should not be used for directly applying the bonding agent to the inner surface of the band if the band has been previously used for a trial fit in the patients mouth, since there is a possibility that cross-contamination may occur when the same syringe is used for a band of a subsequent patient. As a result, it is recommended to dispense the bonding agent of conventional syringes onto a mixing pad, and then use a hand instrument such as a spatula to transfer the bonding agent from the pad to the inner surface of the band.

Unfortunately, the procedure for applying bonding agent to bands as mentioned above is not entirely satisfactory. For one thing, it is rather time consuming to first deposit the bonding agent from the syringe onto the pad and then transfer the bonding agent from the pad to the band. Moreover, once the inner surface of each band has received a sufficient amount of bonding agent, any bonding agent remaining on the pad is considered waste and is discarded.

SUMMARY OF THE INVENTION

The present invention overcomes the disadvantages noted above by provision of a syringe assembly for use in applying a bonding agent to an inner surface of a band. The assembly includes a syringe containing a quantity of the bonding agent as well as a disposable, hollow dispensing tip that is detachably connected to the syringe. The dispensing tip serves as a guide to apply the bonding agent directly to the inner surface of the band in efficient fashion and in a relatively short amount of time.

In more detail, one aspect of the present invention is directed to a method of applying a bonding agent to an inner surface of an orthodontic band. The method includes the act of providing a syringe with an elongated housing having a chamber, a plunger movable in the chamber and a quantity of bonding agent received in the chamber. The method also includes the acts of detachably coupling a dispensing tip having an internal passageway to the syringe, and advancing a plunger of the syringe in the chamber in order to direct the bonding agent from the chamber and through the dispensing tip. The method further includes the act of holding an outlet end of the tip next to an interior space of an orthodontic band in order to dispense the bonding agent moving through the tip directly onto an inner, tooth-facing surface of the band.

Another aspect of the present invention is directed to a syringe assembly that comprises a syringe having an elongated housing with a chamber and a discharge opening in communication with the chamber. The syringe includes a plunger received in the chamber. The syringe also includes a quantity of composition received in the chamber and movable through the discharge opening upon advancement of the piston in the chamber. The assembly also includes a dispensing tip that is detachably coupled to the syringe and has a passageway with a central axis. The passageway is in communication with the discharge opening when the tip is coupled to the syringe. The tip also has an outer end with an outlet opening in communication with the passageway. The outer end extends in a reference plane that lies at an angle in the range of about 15 degrees to about 45 degrees relative to a reference plane normal to the central axis at a location where the central axis meets the outlet opening.

The use of a detachable dispensing tip is a significant advantage, in that the tip can be used to apply the bonding agents to all of the bands of a single patient and then discarded. A new dispensing tip is then applied to the syringe when the syringe is used for applying bonding agent to the bands of a subsequent patient. The detachable dispensing tip therefore reduces the risk of cross-contamination so the likelihood of transferring an infectious disease from one patient to another is diminished.

The dispensing tip also serves as an extension for the syringe, so that application of the bonding agent to the inner surface of the band is facilitated. The tip enables the bonding agent to be applied to the band without the use of a transfer tool such as an applicator or the like. Furthermore, use of the dispensing tip avoids the need to transfer a quantity of the bonding agent from the syringe to a mixing pad so that the wastage of unused bonding agent remaining on the mixing pad after the patient's bands have been sufficiently coated is avoided.

The invention is described in further detail below and is illustrated in the accompanying drawings.

DETAILED DESCRIPTION OF THE PREFERRED EMBODIMENTS

Figure 1:
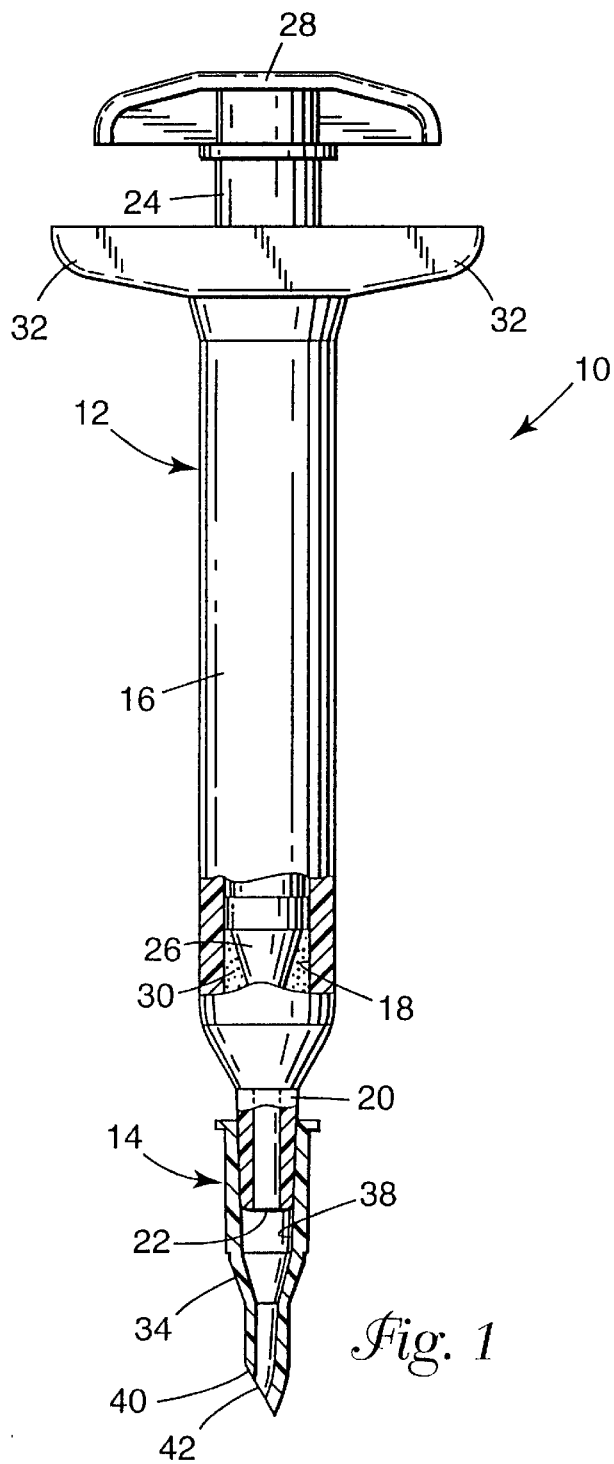
FIG. 1 is a side elevational view in partial section of a dispensing tip and a syringe according to the method and apparatus of certain embodiments of the invention.

A syringe assembly according to the method and apparatus of certain embodiments of the invention is illustrated in FIG. 1 and is broadly designated by the numeral 10. The syringe assembly 10 includes a syringe 12 as well as a dispensing tip 14 that is detachably connected to the syringe 12. The dispensing tip 14 is shown alone in FIGS. 2 and 3.

The syringe 12 includes an elongated housing 16 with inner walls that define an internal chamber 18. The housing 16 and the chamber 18 are generally cylindrical and have an elongated, straight central axis. The housing 16 includes a forward nozzle 20 having a slightly tapered, frustoconical external surface. The nozzle 20 includes a passage that extends from the chamber 18 to a discharge opening 22 that is located on a front end of the nozzle 20.

The syringe 12 includes a plunger 24 that is slidable in the housing 16. The plunger 24 includes a front piston 26 that is slidable in the chamber 18. The plunger 24 also includes a rear, somewhat "T"-shaped handle 28 for facilitating advancement of the plunger 24.

A quantity of bonding agent 30 is received in the chamber 18. When the plunger 24 is advanced, the piston 26 moves in the chamber 18 and forces the bonding agent 30 to move toward the discharge opening 22 of the syringe nozzle 20. A pair of arms 32 are integrally connected to the housing 16 to facilitate holding the syringe 12 by the practitioner's fingers while the practitioner's thumb of the same hand is used to push against the handle 28 and advance the plunger 24 in a forwardly direction.

The bonding agent 30 may be any suitable composition for use when applying an orthodontic band to a tooth. Suitable bonding agents include orthodontic adhesives, cements (including luting cements) and gap-filling materials. A particularly preferred bonding agent is described in applicant's co-pending U.S. patent application entitled "Fluoride Releasing Orthodontic Adhesive", designated U.S. Ser. No. 09/311,606 and filed on even date herewith. Optionally, the bonding agent could be one component of a two component mixture, the other component of which could be pre-applied to the band by the manufacturer or practitioner or applied to the tooth by the practitioner.

Figure 2:
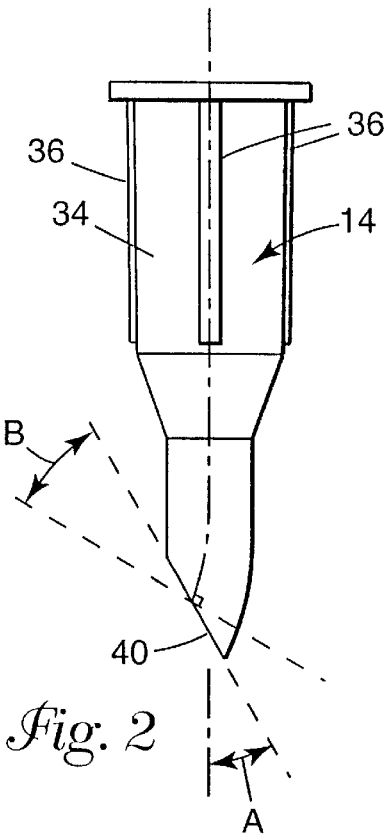
FIG. 2 is an enlarged side elevational view of the dispensing tip alone that is illustrated in FIG. 1.
Figure 3:
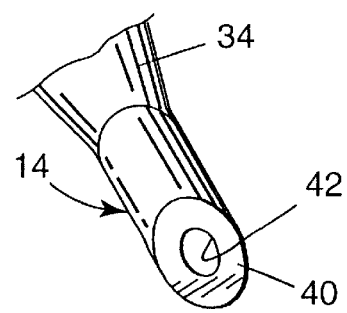
FIG. 3 is a fragmentary side elevational view of the dispensing tip shown in FIG. 2 but viewing the tip in a different direction, and illustrating an outlet opening that is located on an outer end of the tip.

With reference now to FIGS. 2 and 3, the dispensing tip 14 includes a hollow body 34 having a rear portion and a front portion. A series of four ribs 36 are integrally connected to the body 34 and extend along the length of the body 34 for facilitating the users grip on the tip 14 when coupling or uncoupling the tip 14 to the syringe 12. A variety of other grip-enhancing structure on the body 34 may be provided as alternatives.

The dispensing tip 14 includes a central, elongated passageway 38 (see FIG. 1) that has a central axis. When the dispensing tip 14 is coupled to the syringe 12, the passageway 38 is in communication with the discharge opening 22. The passageway 38 extends to an outlet opening 42 that is located on an outer, front end 40 of the dispensing tip 14.

The outer end 40 as well as the outlet opening 42 extend in a reference plane that lies at an angle (designated "A" in FIG. 2) relative to the central reference axis of the rear portion of the body 34 as well as that portion of the passageway 38 that is located in the rear portion of the body 34. Additionally, the reference plane containing the outer end 40 and the outlet opening 42 lies at an angle (designated "B" in FIG. 2) that is other than 90° relative to the central axis of the passageway 38 at a location where the central axis meets the outlet opening 42. Preferably, the reference plane containing the outer end 40 and the outlet opening 42 lies at an angle (designated "B" in FIG. 2) that is in the range of about 10 degrees to about 45 degrees, and more preferably at an angle in the range of about 15 degrees to about 45 degrees, relative to a reference plane that is normal to the central axis at the location where the central axis meets the outlet opening 42. A particularly preferred angle ("B") is 30 degrees.

The inner walls of the body 34 that define the rear portion of the passageway 38 (FIG. 1) preferably have a tapered, frustoconical configuration that matches the frustoconical outer wall of the syringe nozzle 20. As a consequence, the tip 14 can be connected to the syringe 12 by merely placing the nozzle 20 in the passageway 38 and pushing the syringe 12 and the tip 14 in directions toward each other until snugly coupled together by friction fit. If desired, the ribs 36 may be grasped to impart a slight twisting motion to either the tip 14 or the syringe 12 in order to ensure that the tip 14 is securely coupled to the syringe 12. The tip 14 can be disconnected from the syringe 12 when desired by reversing the steps mentioned above.

Other types of structure for coupling the tip 14 to the syringe 12 may also be employed as alternatives to the friction fit, matching taper construction described above. For example, a bayonet-type locking structure may be provided where one of the tip and syringe includes recesses and the other of the tip and syringe includes protruding lugs that are releasably received in the recesses when desired. Other suitable coupling structure can include, for example, mating screw threads on the syringe nozzle and the inner wall of the body. A variety of other types of coupling structure, including Luer-type couplers, will also be apparent to those skilled in the art.

Figure 4:
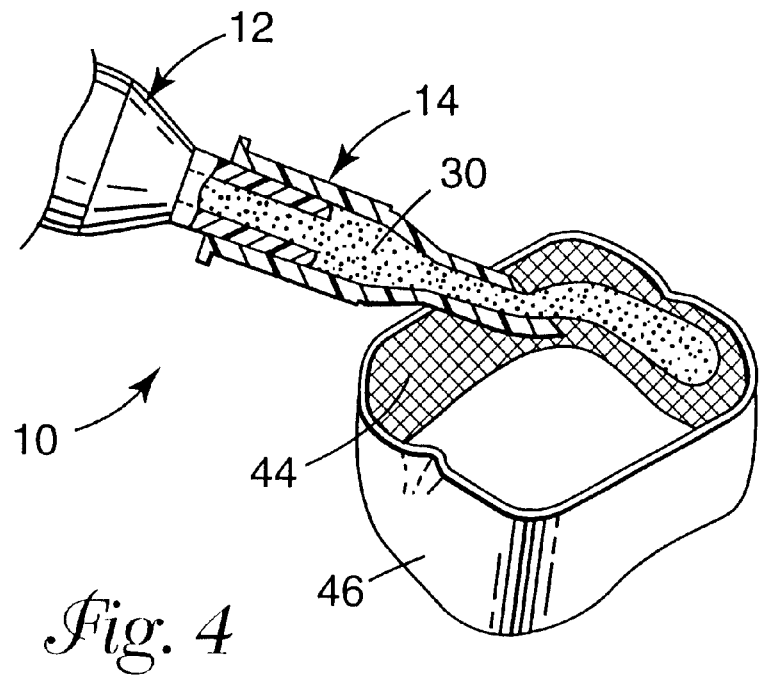
FIG. 4 is a reduced, fragmentary, perspective view of the syringe and dispensing tip shown in FIG. 1 along with an orthodontic band, and showing the act of applying a bonding agent initially contained in the syringe to an inner surface of the band.

FIG. 4 is an illustration of an exemplary use of the assembly 10, where the bonding agent 30 is applied to an inner surface 44 of an orthodontic band 46. When the plunger 24 of the syringe 12 is depressed, the bonding agent 30 is urged through the discharge opening 22 and into the passageway 38 of the dispensing tip 14. Further advancement of the plunger 24 directs the bonding agent 30 through the outlet opening 42, whereupon it is directly deposited onto the inner, tooth-facing surface 44 in a continuous bead or ribbon. Advantageously, one hand of the user may be used to grasp the syringe 12 and depress the plunger 24 in order to dispense the bonding agent 30 while the other hand of the user may be utilized to grasp the band 46 and to rotate the band 46 as needed along a generally circular path in order to provide a continuous ribbon of bonding agent 30 to the entire inner peripheral surface 44 of the band 46.

Advantageously, the dispensing tip 14 serves as a convenient extension for the syringe 12 in order to facilitate placing the bonding agent 30 directly onto the inner band surface 44. Moreover, the application of the bonding agent 30 to the inner surface 44 is enhanced by the angular orientation of the outer end 40 and the outlet opening 42 relative to the central axis of the discharge tip passageway 38 at the opening 42 as described above. That angular orientation helps to ensure that the cross-sectional shape of the ribbon of bonding agent 30 applied to the inner surface 44 initially has an oval-shaped configuration, so that satisfactory coverage of the bonding agent 30 on the inner surface 44 is assured. As another option, the outlet opening 42 may alternatively have a circular configuration.

During dispensing, the outer end 40 is held next to or in contact with the inner surface 44. The angular orientation mentioned above facilitates placement of the outer end 40 on the inner surface 44, especially as the band 46 is manipulated by the practitioner. As the bonding agent 30 is discharged from the outlet opening 42, the inner surface 44 serves as a baffle and helps to spread the bonding agent 30 in lateral directions (i.e., in directions parallel to the central axis of the band 46). The angular orientation of the outer end 40 and the outlet opening 42, along with the curved axis of the tip 14, helps to provide good visibility by the practitioner of the dispensing operation to ensure that a sufficient layer of bonding agent 30 is present.

In use, the assembly 10 is typically used to apply bonding agent 30 to all of the orthodontic bands 46 that have been selected for use with a single patient. Normally, the bands 46 would be selected by first fitting by trial and error a number of bands 46 on each tooth to receive a band 46 and then selecting the bands 46 that provide the best fit. Since the tip 14 may come into contact with the bands 46 that have been previously in the patient's oral cavity for the trial fitting, the tip 14 is discarded after all of the bands 46 selected for the patient have been coated with a bead or ribbon of bonding agent 30.

The nozzle 20 of the syringe 12 is normally covered with a cap (not shown) once all the bands 46 chosen for a particular patient have received the bonding agent 30. Preferably, the syringe chamber 18 has sufficient capacity to contain an amount of bonding agent 30 for coating all of the bands 46 of several patients. As such, a new dispensing tip 14 is coupled to the syringe 12 whenever the latter is utilized in connection with a subsequent patient so that the risk of cross-contamination is reduced.

The syringe 12 and the dispensing tip 14 may be made of any suitable material including a number of plastics. A suitable plastic material is black polypropylene, although a variety of other materials may also be employed.

Figure 5:
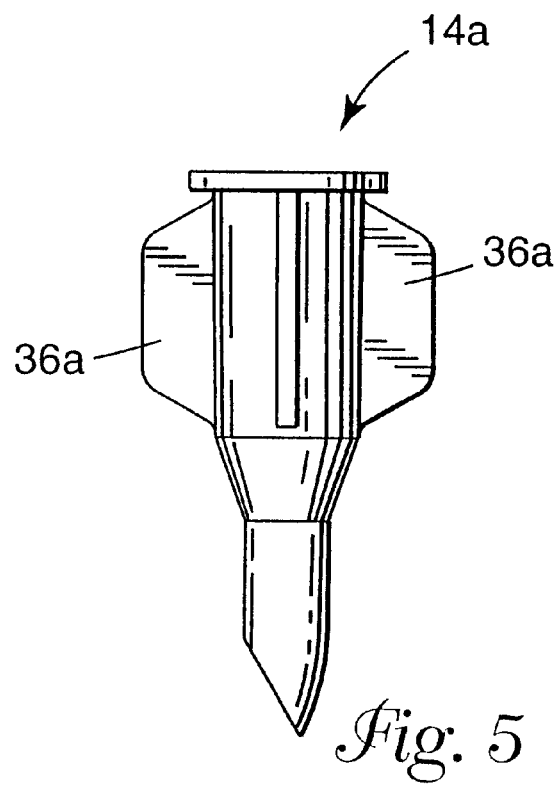
FIG. 5 is a side elevational view of a dispensing tip in accordance with another embodiment of the invention.

FIG. 5 is an illustration of dispensing tip 14a according to another embodiment of the invention. The dispensing tip 14a is essentially the same as the dispensing tip 14 described above, except that the tip 14a includes a plurality (such as two or four) radially-extending, external ribs 36a that are much larger than the ribs 36 of the tip 14. The increased surface area provided by the ribs 36a facilitates grasping and/or rotating of the tip 14a in order to ease coupling and uncoupling of the tip 14a from the syringe 12 when desired.

Those skilled in the art will recognize that a variety of modifications and additions may be provided. For example, the syringe could be a double-barrel syringe with dual dispensing chambers for containing two initially separate components of a two-component adhesive. The dispensing tip for use with such a syringe could optionally contain a mixing element in order to facilitate mixing of the components during a dispensing operation.

Moreover, other types of syringes may be used as alternatives to the syringe 12 described above. An example of a suitable syringe is a pistol-shaped applicator such as the applicator described in U.S. Pat. No. 5,743,436, which is incorporated by reference herein. Those types of applicators may be desired in instances where a mechanical advantage provided by a pivoting lever arm would facilitate dispensing of the bonding agent.

As another option, the bonding agent could be received in a cartridge, which is detachably received in the syringe. In that instance, the cartridge walls serve as a housing with a chamber for receiving bonding agent, and the cartridge is replaced when empty.

A number of other modifications and additions are also possible. Consequently, the invention should not be deemed limited to the specific, presently preferred embodiments that are described in detail above, but instead only by a fair scope of the claims that follow along with their equivalents.

What is claimed is:

1. A method of applying a bonding agent to an inner surface of an orthodontic band comprising the acts of:

providing a syringe with an elongated housing having a chamber, a plunger movable in the chamber and a quantity of bonding agent received in the chamber;

detachably coupling a dispensing tip having an internal passageway to the syringe;

advancing a plunger of the syringe in the chamber in order to direct the bonding agent from the chamber and through the dispensing tip; and holding an outlet end of the tip next to an interior space of an orthodontic band in order to dispense the bonding agent moving through the tip directly onto an inner, tooth-facing surface of the band.

2. The method of claim 1, wherein the act of providing the syringe includes the act of providing a syringe with a quantity of bonding agent sufficient for use with multiple patients.

3. The method of claim 2, and including the act of replacing the tip between patients.

4. The method of claim 1, and including the act of rotating the band with one hand while holding the syringe with the other hand in order to deposit a continuous bead of bonding agent along the entire periphery of the inner surface of the band.

5. The method of claim 1, wherein the act of detachably coupling a dispensing tip to the syringe includes the act of moving a nozzle of the syringe into a rear portion of the dispensing tip.

6. The method of claim 5, wherein the act of detachably coupling a dispensing tip to the syringe is carried out by use of a friction fit.

7. The method of claim 1, wherein the act of detachably coupling a dispensing tip to the syringe includes the act of moving a tapered outer surface of a nozzle of the syringe into snug contact with an inner tapered surface of the dispensing tip.

8. The method of claim 1, and including the act of providing a tip having an outer end with an outlet opening that extends in a reference plane that lies at an angle in the range of about 15 degrees to about 45 degrees relative to a reference plane normal to a central axis of the passageway at a location where the central axis meets the outlet opening, and wherein the act of holding an outlet end of the tip next to an interior space of an orthodontic band in order to dispense the bonding agent includes the act of dispensing a ribbon of the bonding agent, wherein the ribbon has an oval-shaped cross-sectional configuration.

9. The method of claim 1, wherein the act of advancing a plunger of the syringe in the chamber is carried out by pushing the plunger in a forward direction toward the dispensing tip.

10. The method of claim 1, wherein the act of detachably coupling a dispensing tip to the syringe includes the act of grasping a plurality of ribs of the dispensing tip.

* * * * *